(12) United States Patent
Swiecicki et al.

(10) Patent No.: US 7,931,634 B2
(45) Date of Patent: Apr. 26, 2011

(54) BODILY EXUDATE CAPTURING ARTICLE

(75) Inventors: Alethea Angelic Marie Swiecicki, Greenville, WI (US); Cindy Lou Price, Appleton, WI (US); MaryAnn Zunker, Oshkosh, WI (US); Richard Joseph Hantke, Appleton, WI (US); Corey James Pelz, Franklin, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1003 days.

(21) Appl. No.: 10/742,236

(22) Filed: Dec. 18, 2003

(65) Prior Publication Data

US 2005/0137557 A1    Jun. 23, 2005

(51) Int. Cl.
*A61F 13/15* (2006.01)
*A61F 13/20* (2006.01)
*A61F 5/44* (2006.01)

(52) U.S. Cl. .................... 604/385.17; 604/329
(58) Field of Classification Search .......... 604/329–330, 604/346, 354, 385.01, 385.17; D24/124, D24/125
See application file for complete search history.

(56) References Cited

U.S. PATENT DOCUMENTS

| | | | | |
|---|---|---|---|---|
| 976,883 A * | 11/1910 | Keagy et al. | .................. | 604/354 |
| 3,194,238 A | 7/1965 | Breece, Jr. | | |
| 3,349,768 A | 10/1967 | Keane | | |
| 3,512,185 A * | 5/1970 | Ellis | ............................ | 604/329 |
| 3,722,503 A * | 3/1973 | Hovick | ......................... | 600/574 |
| 3,726,277 A | 4/1973 | Hirschman | | |
| 3,983,873 A | 10/1976 | Hirschman | | |
| 4,061,145 A | 12/1977 | Desmarais | | |
| 4,194,508 A | 3/1980 | Anderson | | |
| 4,246,901 A * | 1/1981 | Frosch et al. | ................. | 604/329 |
| 4,421,511 A | 12/1983 | Steer et al. | | |
| 4,457,314 A * | 7/1984 | Knowles | ....................... | 600/573 |
| 4,475,911 A | 10/1984 | Gellert | | |
| 4,496,355 A | 1/1985 | Hall et al. | | |
| 4,568,339 A | 2/1986 | Steer | | |

(Continued)

FOREIGN PATENT DOCUMENTS

EP    0 966 937 A1    12/1999

(Continued)

OTHER PUBLICATIONS

Gray, Henry, *Anatomy of the Human Body*, vol. II, Thirtieth American Edition, published by Lea and Febiger, 1985, pp. 1571-1581.

*Primary Examiner* — Melanie J Hand
(74) *Attorney, Agent, or Firm* — Ralph H. Dean; David J. Arteman

(57) ABSTRACT

A disposable intralabial urinary incontinence article having a resilient and liquid impermeable exostructure captures bodily exudates. The exostructure has a top surface and an internal space adapted to receive fluids. At least a portion of the exostructure is a flange that rests at least partially outside the labia. The exostructure also has a neck extending from the top surface that at least partially occupies the vestibular region and rests proximate the vestibule floor. The neck has a fluid receiving opening which is in communication with the internal space. The neck is configured so the fluid receiving opening is positioned generally adjacent the urethral meatus to direct urine into the internal space. The internal space may include an absorbent and the article may include a clitoral guide to aid positioning of the article within the vestibule.

17 Claims, 8 Drawing Sheets

U.S. PATENT DOCUMENTS

| | | | | |
|---|---|---|---|---|
| 4,610,675 | A | 9/1986 | Triunfol | |
| 4,627,848 | A | 12/1986 | Lassen et al. | |
| 4,681,572 | A | 7/1987 | Tokarz et al. | |
| 4,681,577 | A | 7/1987 | Stern et al. | |
| 4,685,914 | A | 8/1987 | Holtman | |
| 4,692,160 | A | 9/1987 | Nussbaumer | |
| 4,753,644 | A | 6/1988 | Cottenden et al. | |
| 4,781,713 | A | 11/1988 | Welch et al. | |
| 4,846,819 | A | 7/1989 | Welch | |
| 4,846,824 | A | 7/1989 | Lassen et al. | |
| 4,886,508 | A * | 12/1989 | Washington | 604/327 |
| 4,889,533 | A | 12/1989 | Beecher | |
| 4,911,698 | A | 3/1990 | Wapner | |
| 4,914,957 | A | 4/1990 | Dougherty | |
| 4,936,838 | A | 6/1990 | Cross et al. | |
| 5,074,855 | A | 12/1991 | Rosenbluth et al. | |
| 5,171,302 | A | 12/1992 | Buell | |
| 5,234,409 | A | 8/1993 | Goldberg et al. | |
| 5,247,072 | A | 9/1993 | Ning et al. | |
| 5,290,262 | A | 3/1994 | Vukos et al. | |
| 5,300,055 | A | 4/1994 | Buell | |
| 5,336,208 | A | 8/1994 | Rosenbluth et al. | |
| 5,383,868 | A | 1/1995 | Hyun | |
| 5,389,181 | A | 2/1995 | Vukos et al. | |
| 5,484,429 | A | 1/1996 | Vukos et al. | |
| 5,520,675 | A | 5/1996 | Knox-Sigh | |
| 5,559,165 | A | 9/1996 | Paul | |
| 5,591,150 | A | 1/1997 | Olsen et al. | |
| 5,658,270 | A | 8/1997 | Lichstein | |
| 5,672,165 | A | 9/1997 | Belecky et al. | |
| 5,752,525 | A | 5/1998 | Simon et al. | |
| 5,769,091 | A | 6/1998 | Simon et al. | |
| 5,786,395 | A | 7/1998 | Stone et al. | |
| 5,873,869 | A | 2/1999 | Hammons et al. | |
| 5,885,265 | A | 3/1999 | Osborn, III et al. | |
| 5,891,126 | A | 4/1999 | Osborn, III et al. | |
| 5,893,176 | A | 4/1999 | Magiera et al. | |
| 5,895,349 | A | 4/1999 | Tihon | |
| 5,895,381 | A | 4/1999 | Osborn, III | |
| 5,916,205 | A | 6/1999 | Olson et al. | |
| 5,927,282 | A | 7/1999 | Lenker et al. | |
| 5,928,452 | A | 7/1999 | McFall et al. | |
| 5,947,943 | A * | 9/1999 | Lee | 604/361 |
| 5,964,689 | A | 10/1999 | McFall et al. | |
| 5,968,026 | A | 10/1999 | Osborn, III et al. | |
| 6,056,687 | A | 5/2000 | Polyak et al. | |
| 6,131,736 | A | 10/2000 | Farris et al. | |
| 6,152,905 | A | 11/2000 | Osborn, III et al. | |
| 6,183,456 | B1 | 2/2001 | Brown et al. | |
| 6,203,512 | B1 | 3/2001 | Farris et al. | |
| 6,213,993 | B1 | 4/2001 | Zacharias et al. | |
| 6,258,074 | B1 | 7/2001 | Prazak | |
| 6,261,679 | B1 | 7/2001 | Chen et al. | |
| 6,297,424 | B1 | 10/2001 | Olson et al. | |
| 6,319,238 | B1 | 11/2001 | Sartorio et al. | |
| 6,341,377 | B1 | 1/2002 | Faries et al. | |
| 6,355,022 | B1 | 3/2002 | Osborn, III et al. | |
| 6,406,648 | B1 | 6/2002 | Noel et al. | |
| 6,416,501 | B2 | 7/2002 | Brown et al. | |
| 6,551,292 | B1 * | 4/2003 | D'Acchioli et al. | 604/329 |
| 6,592,560 | B2 * | 7/2003 | Snyder | 604/331 |
| 2002/0016579 | A1 * | 2/2002 | Stenberg | 604/361 |

FOREIGN PATENT DOCUMENTS

| | | |
|---|---|---|
| GB | 1 253 497 A | 11/1971 |
| GB | 2 184 023 A | 6/1987 |
| WO | WO 93/04633 A1 | 3/1993 |
| WO | WO 95/16424 A1 | 6/1995 |
| WO | WO 99/01094 A1 | 1/1999 |
| WO | WO 99/48451 A1 | 9/1999 |
| WO | WO 99/55269 A1 | 11/1999 |
| WO | WO 99/56681 A2 | 11/1999 |
| WO | WO 99/56689 A1 | 11/1999 |
| WO | WO 00/00116 A1 | 1/2000 |
| WO | WO 00/40197 A1 | 7/2000 |
| WO | WO 01/21227 A1 | 3/2001 |
| WO | WO 01/54633 A1 | 8/2001 |
| WO | WO 0154633 A1 * | 8/2001 |
| WO | WO 01/82985 A2 | 11/2001 |
| WO | WO 01/85073 A1 | 11/2001 |
| WO | WO 02/13750 A2 | 2/2002 |
| WO | WO 02/34180 A1 | 5/2002 |
| WO | WO 02/41817 A1 | 5/2002 |
| WO | WO 02/41818 A1 | 5/2002 |
| WO | WO 02/058611 A1 | 8/2002 |
| WO | WO 02/094155 A1 | 11/2002 |
| WO | WO 02/100308 A2 | 12/2002 |
| WO | WO 02/100312 A2 | 12/2002 |
| WO | WO 02/100313 A2 | 12/2002 |
| WO | WO 02/100314 A1 | 12/2002 |
| WO | WO 02/100315 A1 | 12/2002 |
| WO | WO 02/102424 A1 | 12/2002 |

* cited by examiner

BODILY EXUDATE CAPTURING ARTICLE

BACKGROUND

Conventional bodily exudate capture articles, such as feminine urinary incontinence articles, can be broadly categorized as disposable or extended-use. The extended-use articles generally capture and store urine and other exudates until such time as the user or caregiver removes and empties the article. Extended-use articles are designed to receive more than one urine insult and/or exudate discharge and are designed to be cleaned and reused many times over a prolonged period of time. Such articles may have various attachment means or alignment means to decrease the likelihood of leakage. For example, some extended-use articles use an intra-vaginal tab to assist alignment of the article. Other extended-use articles incorporate adhesives or suction to protect against urine leaks. However, many extended-use exudate capture articles are undesirable because users do not want to clean the articles between uses. Also, the size and cumbersomeness of currently available articles fail to provide the discretion or ease of use desired by users of such articles. Finally, internal alignment devices, such as intra-vaginal tabs, can be physically and emotionally uncomfortable for users.

The other general type of bodily exudate capture articles, the disposable articles, are generally absorbent articles that are discarded when soiled. Such articles are designed for a single or limited wear to manage one or more urine insults or exudate discharges before disposal. This category of urinary incontinence articles can include internal articles, external articles, or intralabial articles. Disposable articles may be occlusive articles designed to prohibit the flow of urine from the urethral opening or meatus. For example, adhesive backed occluding articles may be inserted directly into or over the urethral opening to stop the flow of urine from the bladder to the outside of the body via the urethra. However, some women are not comfortable with an internally placed urinary incontinence article or use of such an article is otherwise undesirable. Other women may not be comfortable using an article that uses adhesive to attach over the urethral opening. In such situations, the user may choose between an external article and an intralabial article. The external articles are generally absorbent pads or liners used to absorb urine after it has exited the body. This type of urinary incontinence article has the advantage of external use, but it too can be uncomfortable and lack discretion due to its size and location external to the body. The third type of urinary incontinence article, the intralabial article, is generally positioned between the user's labia and is configured to absorb urine as it exits from the body. This type of urinary incontinence article has the advantage of greater discretion because of the smaller size and closer positioning to the body, however, the small size increases the possibility of leakage occurring due to decreased capacity. The small size also increases the chances of product failure due to improper placement. Ideally, the labial article would be consistently positioned close enough to the urethral opening to ensure the absorbent article captures the urine discharge as it leaves the urethral opening. However, many women are not familiar with their own anatomy and specifically the location of the urethral opening. Furthermore, many women are not comfortable looking at or feeling their genital region for the proper placement of the labial article. Therefore, improper placement of traditional intralabial articles relative to the urethral opening is more likely to occur.

Even women that are successful in finding the urethral opening and positioning the article may still have leakage of urine. Traditional articles are generally configured to receive urine discharges upon a top surface and are designed to absorb urine through the top surface. Despite the absorbent qualities of such articles, urine may still run off the top surface before the labial article can fully absorb the urine. Therefore, it is apparent that there is a need for an intralabial bodily exudate capture article that is discrete, easy to position without the need to search for the urethral opening or without the need to insert portions of the device into the body, directs urine into the exudate capture article and is disposable.

SUMMARY

In response to the discussed difficulties and problems encountered previously, the present invention relates generally to a disposable bodily exudate capturing article. The invention more particularly provides a disposable intralabial urinary incontinence article including a resilient and liquid impermeable exostructure. The exostructure has a top surface, a bottom surface, and an internal space adapted to receive fluids. At least a portion of the exostructure includes a flange. The flange is configured to rest at least partially outside the labia of a female wearer. The exostructure also includes a neck extending from the top surface. The neck is adapted to at least partially occupy the vestibular region of the wearer and is configured to rest close to the wearer's vestibule floor. The neck has a fluid receiving opening in communication with the internal space and is configured so the fluid receiving opening is positioned generally adjacent to the wearer's urethral meatus. When the intralabial urinary incontinence article is so positioned, the urine exiting the body of the wearer is directed through the fluid receiving opening, through the neck and into the internal space of the exostructure.

In various embodiments of the present invention, the disposable intralabial urinary incontinence article includes an absorbent disposed within the internal space of the liquid impermeable exostructure. The absorbent can be made from cellulose, super absorbent polymer, open cell foam, open cell polymeric foam, absorbent polymer films, or combinations of these materials. In various embodiments, the absorbent is removable.

In various embodiments, the exostructure may be made from silicone, silicone composite, silicone elastomer, polyurethanes, closed cell foam, open cell foam, natural rubber or combinations of these materials. The exostructure may be made of resilient materials to resist distortion during use.

In various embodiments, the exostructure has a posterior portion and the top surface has a decreasing slope in the posterior portion to accommodate the region between the posterior commissure of labia and anus.

In various embodiments, the fluid receiving opening is at least partially circumscribed by a defining ring. The defining ring may be resilient and thus able to resist labial crushing.

In various embodiments, the disposable intralabial urinary incontinence article includes a shroud, a body adhesive, or both. In some embodiments, the intralabial urinary incontinence article has a one-way valve. The one-way valve may be disposed within the internal space of the exostructure at various locations. The one-way valve divides the internal space into at least one first region and at least one second region and allows fluid to pass from the first region into the second region but prevents fluid from passing from the second region into the first region.

In various embodiments, the neck of the disposable intralabial incontinence article has a clitoral guide. The clitoral guide is adapted to coordinate with a wearer's clitoris and assist the wearer to properly position the neck so the fluid receiving opening is generally adjacent the wearer's urethral meatus. In some embodiments, the clitoral guide is an extension of the neck that is adapted to surround the clitoris and rest in contact with the wearer's prepuce of clitoris. The clitoral guide, in alternative embodiments, is formed by a notch in the neck adapted to abut the wearer's clitoris.

In various embodiments, the fluid receiving opening is sized to span the wearer's urethra meatus and vaginal orifice to capture vaginal discharge, menses, urine, or other bodily exudates.

In various embodiments, the intralabial urinary incontinence article includes a wetness indicator.

In some embodiments, the disposable intralabial incontinence article includes an absorbent within the internal space, the fluid receiving opening is at least partially circumscribed by a defining ring that is resilient and is adapted to resist labial crushing, the exostructure has a posterior portion and the top surface has a decreasing slope in the posterior portion to accommodate the region between the posterior commissure of labia and anus, and the neck includes a clitoral guide adapted to coordinate with a wearer's clitoris and assist the wearer to properly position the neck so the fluid receiving opening is generally adjacent the wearer's urethral meatus.

The present invention also provides a method of providing a system to capture urine. The system includes providing a disposable intralabial urinary incontinence article including a resilient and liquid impermeable exostructure. The exostructure has a top surface and an internal space adapted to receive fluids. At least a portion of the exostructure includes a flange. The flange is configured to rest at least partially outside the labia of a female wearer. The exostructure also includes a neck extending from the top surface. The neck is adapted to at least partially occupy the vestibular region of the wearer and the neck is configured to rest close to the wearer's vestibule floor. The neck has a fluid receiving opening in communication with the internal space. The neck is configured so the fluid receiving opening is positioned generally adjacent to the wearer's urethral meatus. When the intralabial urinary incontinence article is so positioned, the urine exiting the body of the wearer is directed through the fluid receiving opening, through the neck and into the internal space of the exostructure. The method also includes providing instructions to a female wearer to position the intralabial urinary incontinence article such that the neck at least partially occupies the wearer's vestibular area and the fluid receiving opening rests proximate the wearer's urethral meatus. Finally, the method includes enabling the wearer to successfully direct urine towards the internal space by following the instructions provided.

The present invention also provides a method of providing a system to accurately position an intralabial urinary incontinence article. The method includes providing an intralabial urinary incontinence article with a resilient and liquid impermeable exostructure. The exostructure has a top surface and an internal space which is adapted to receive fluids. At least a portion of the exostructure includes a flange. The flange is configured to rest at least partially outside the labia of a female wearer. The exostructure also includes a neck extending from the top surface. The neck is adapted to at least partially occupy the vestibular region of the wearer and the neck is configured to rest close to the wearer's vestibule floor. The neck has a fluid receiving opening in communication with the internal space. The neck is configured so the fluid receiving opening is positioned generally adjacent to the wearer's urethral meatus. The neck is further configured to include a clitoral guide. The method further includes providing instructions to a female wearer to position the intralabial urinary incontinence article such that the clitoral guide engages the wearer's clitoris. Finally, the method includes enabling the wearer, by following the instructions provided, to successfully position the intralabial urinary incontinence article at least partially within the wearer's vestibule such that the fluid receiving opening is proximate the wearer's urethral meatus.

FIGURES

DETAILED DESCRIPTION

Figure 1:
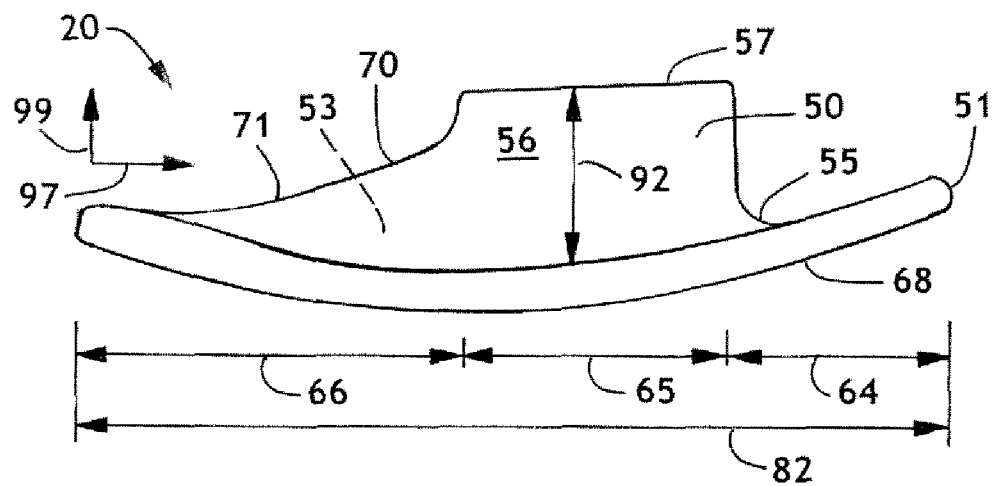
FIG. 1 illustrates a side view of one embodiment of an exemplary bodily exudate capturing article.
Figure 7:
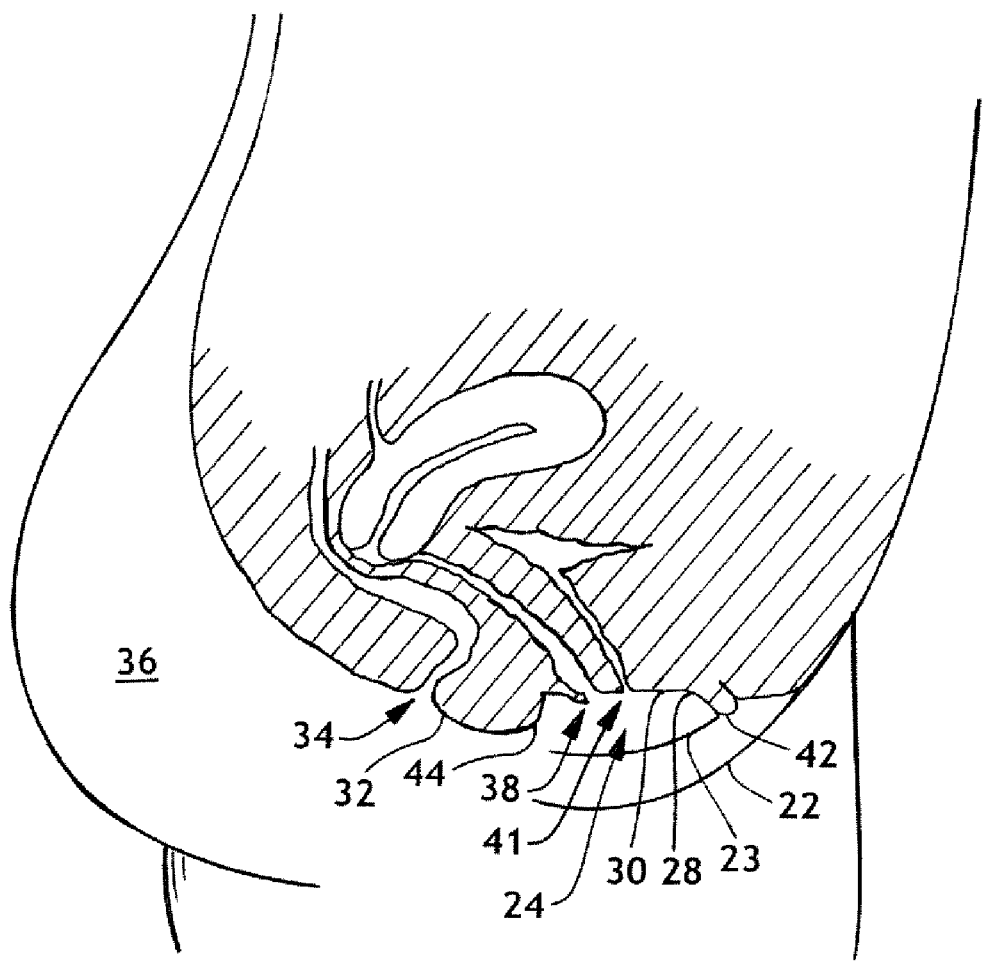
FIG. 7 illustrates a sagittal view of the female anatomy.
Figure 8:
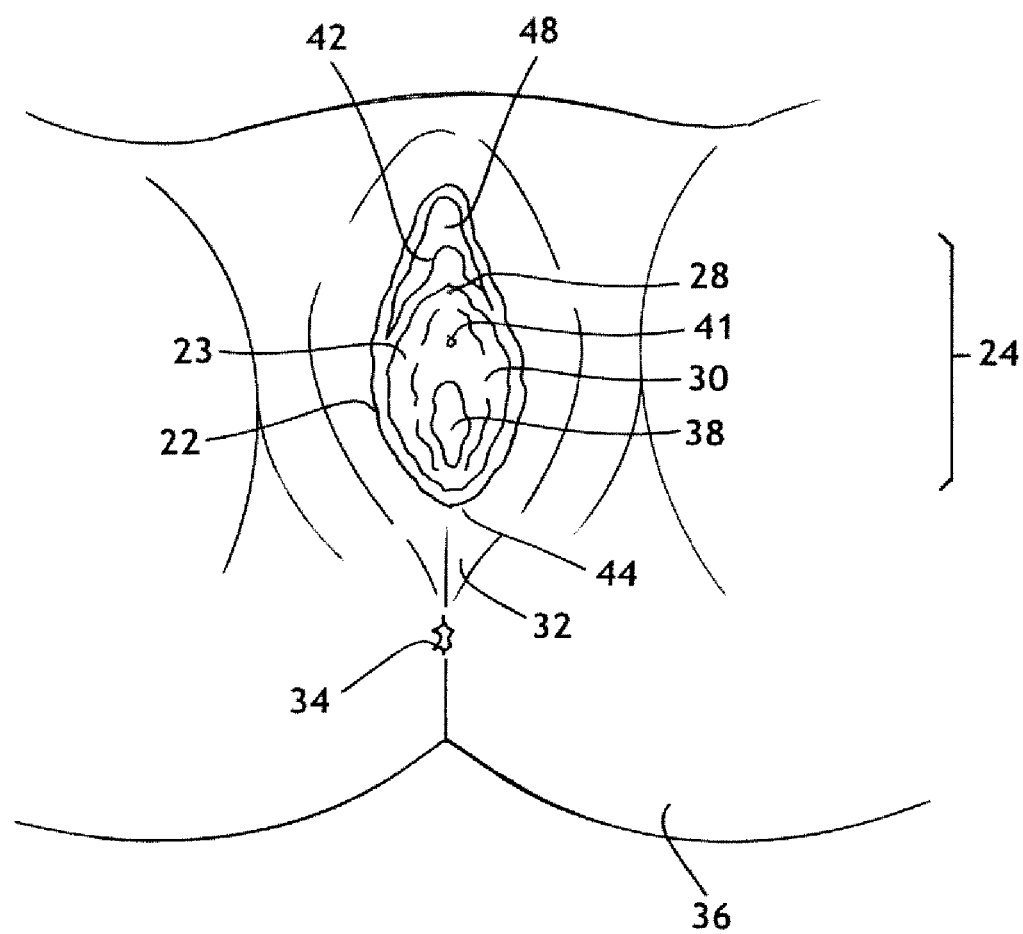
FIG. 8 illustrates the external genitalia of a typical female.

The present invention is directed to a disposable bodily exudate capturing article. For example, the present invention may be an article used to capture urine, menses, or other bodily exudates such as vaginal discharge. As used herein, the term "disposable" refers to an article designed to be used a limited number of times and then thrown away. Disposable articles are not intended to be laundered, sanitized or otherwise restored for reuse and therefore can be discarded after a single use. However, emptying, rinsing and/or repositioning a product a limited number of times, for example 2, 3, or 4 times, during a short period of time, for example, 24 hours or less, before discarding the article would still be considered a single use and thus "disposable." For purposes of the detailed description herein, a female urinary incontinence article will be described with reference to FIGS. 1-8, in which similar parts are identified with like reference characters. FIG. 1 is an illustration of an intralabial urinary incontinence article, designated generally as 20. FIG. 7 representatively illustrates a sagittal view of the female anatomy, whereas FIG. 8 representatively illustrates the external female genitalia. The intralabial urinary incontinence article 20 may be configured to reside at least partially within a wearer's vestibular region, designated generally as 24 as representatively illustrated in FIGS. 7 and 8. As used herein, the term "intralabial urinary incontinence article" refers to an article which is specifically configured for disposition in between a wearer's labia majora 22, extending at least partially into a female wearer's vestibule 24 during use and adapted to capture urine. For example, an intralabial urinary incontinence article may extend at least about 40% of the depth and width and length of the vestibule 24. In further examples an intralabial urinary incontinence article may extend at least about 50%, at least about 60%, at least about 70%, at least about 80%, at least about 90%, or about 100% of the depth and width and length of the vestibule 24. An intralabial urinary incontinence article may extend from the wearer's labial area, but most of the article is disposed between the labia majora 22 and/or the vestibule 24.

For purposes of the ensuing description, the vestibule 24 is considered to be the region defined within the labia beginning at about a point known as the anterior aspect of vestibule 28, extending rearward to the posterior labial commissure 44 and bounded inwardly by the floor 30 of the vestibule 24. One of skill in the art fully understands that there is a wide range of variation among women with respect to the relative size and shape of labia majora 22 and labiaminora 23 as the same interrelatedly define the contour of the vestibule 24. For purposes of the present description, however, such differences will not specifically be addressed, it being recognized that in any event the disposition of the urinary incontinence article 20 into the vestibule 24 will necessitate placement between the labia majora 22 regardless of any such consideration respecting the labiaminora 23. Lying caudally of the vestibule 24 is the perineum 32, which leads to the anus 34 in the region of the buttocks 36. Within the vestibule 24 itself is located the principal urogenital members which, for purposes pertinent here, are constituted of the vaginal orifice 38 and the urethral meatus 41. The clitoris 42 lies proximal to the anterior end of the vestibule 24 and is covered by the prepuce of the clitoris 48. Given the foregoing simplified review of this anatomical region, and to facilitate the present description, the vestibule 24 will be considered generally to be the region between the posterior labial commissure 44 and the anterior aspect of vestibule 28, for convenience. For a more comprehensive description of this portion of the human female anatomy, however, attention is invited to *Anatomy of the Human Body* by Henry Gray, Thirtieth American Edition (Carmine D. Clemente ed., Lea & Febiger, 1985) at 1571-1581.

Figure 7A:
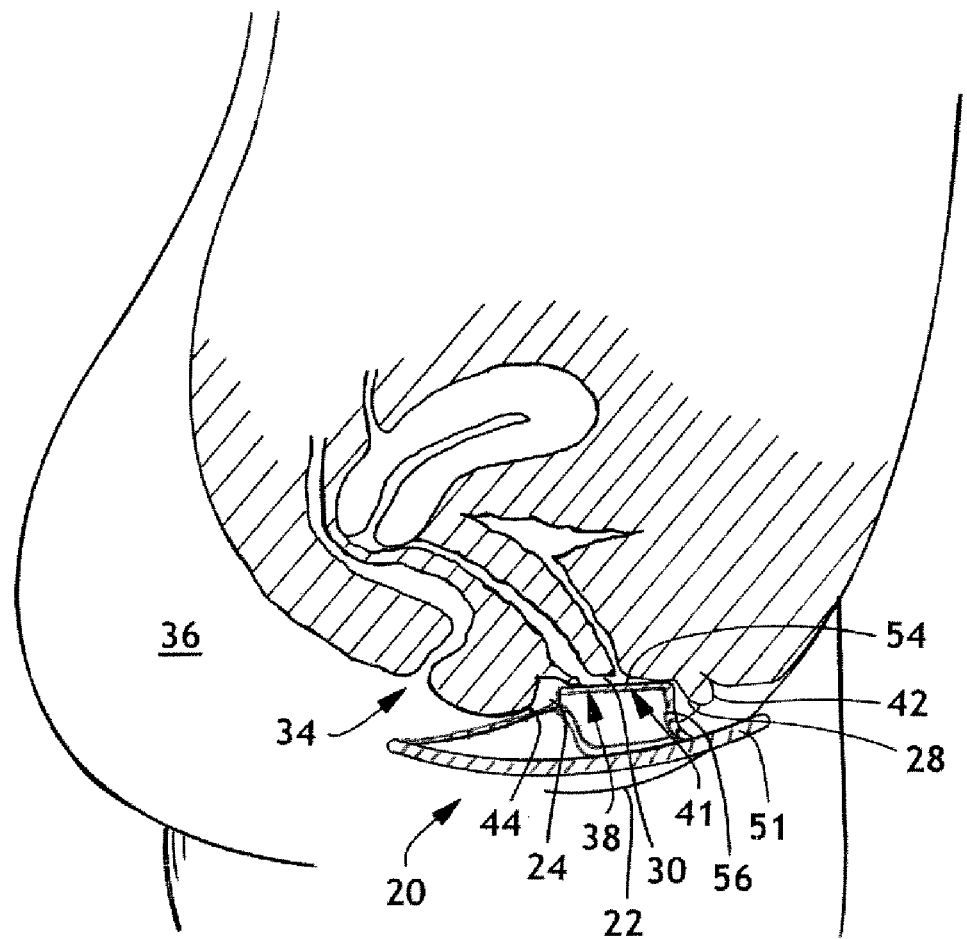
FIG. 7A illustrates a sagittal view of the female anatomy with a representative placement of one embodiment of an exemplary bodily exudate capturing article.
Figure 7B:
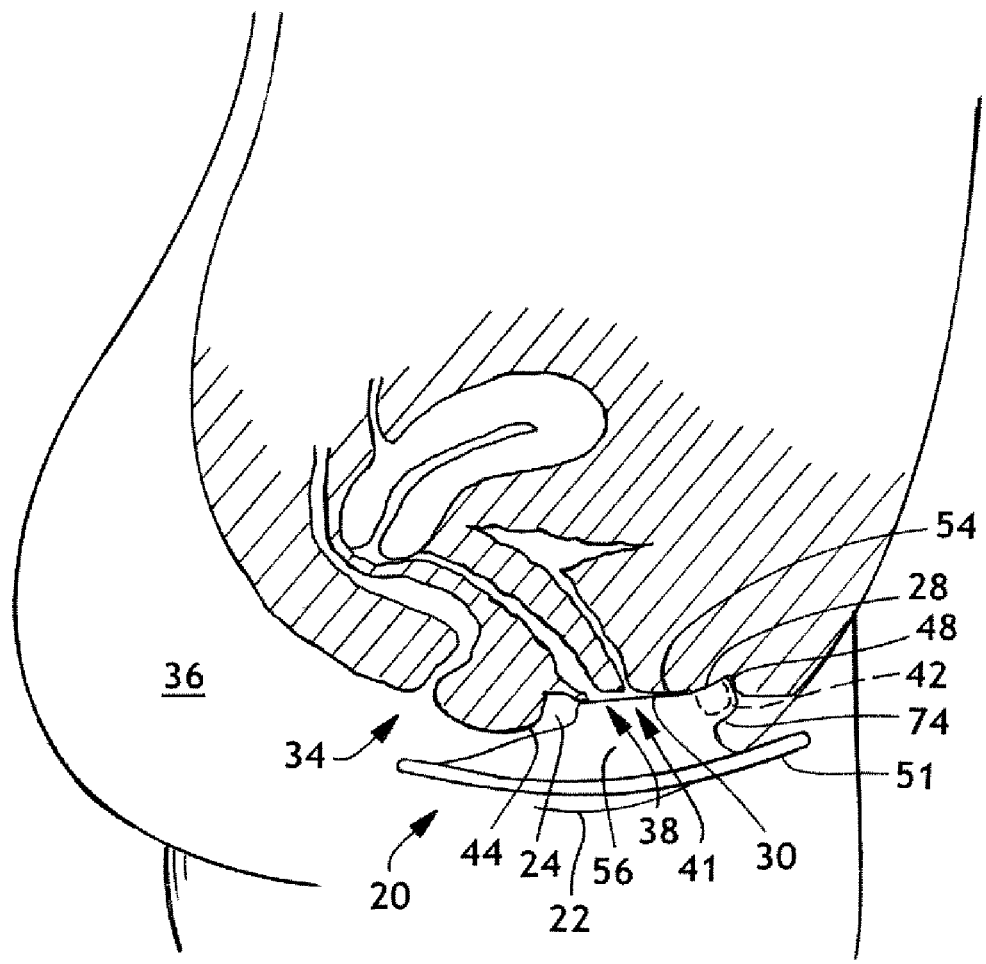
FIG. 7B illustrates a sagittal view of the female anatomy with a representative placement of one embodiment of an exemplary bodily exudate capturing article.
Figure 7C:
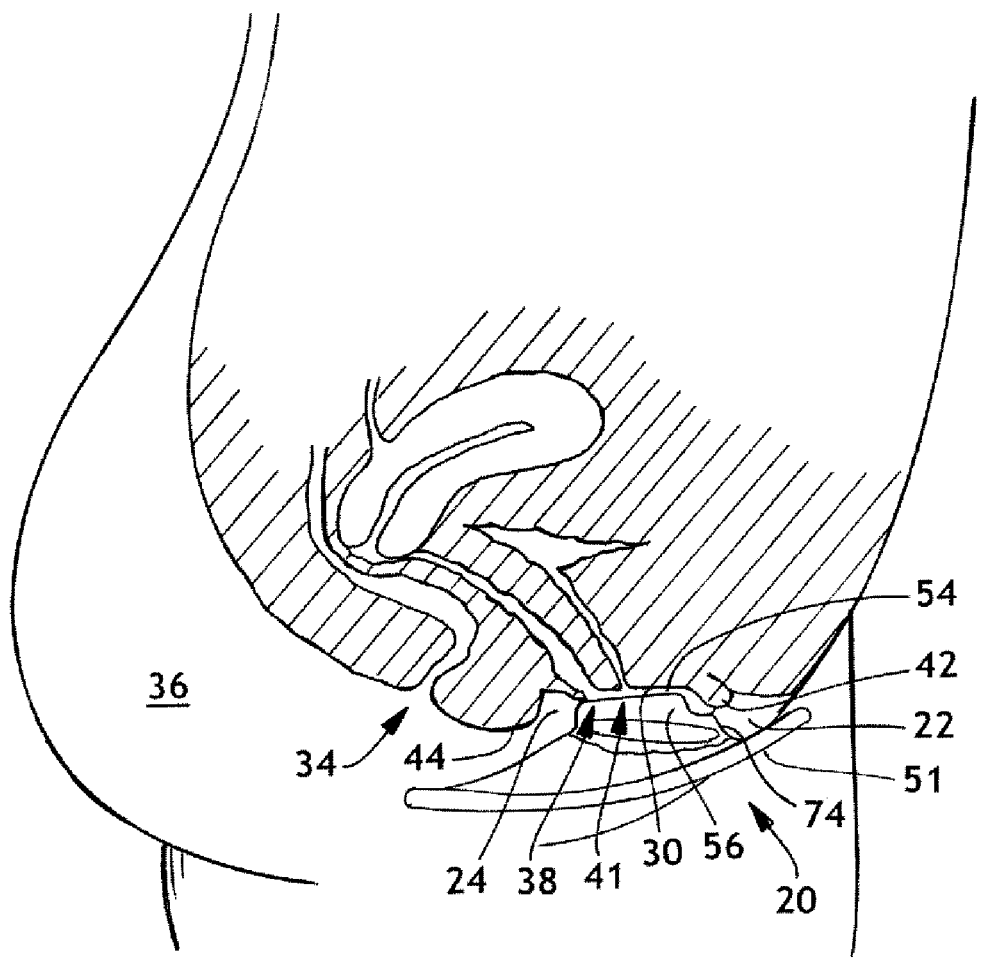
FIG. 7C illustrates a sagittal view of the female anatomy with a representative placement of one embodiment of an exemplary bodily exudate capturing article.

As can be seen with reference to the anatomical structure illustrated in FIGS. 7A, 7B, and 7C the urinary incontinence article 20 is disposed at least partially within the vestibule 24 proximate the urethral meatus 41 to capture urine flow therefrom. In this regard, the predominant uses of the urinary incontinence article 20 are for the capture and, in some embodiments, the absorption of urine as occurs with involuntary discharge of urine in females. As will be apparent to those skilled in the art, the urinary incontinence article 20 may also be used to capture and additionally absorb other body exudates, such as menses and vaginal discharges.

Figure 2:
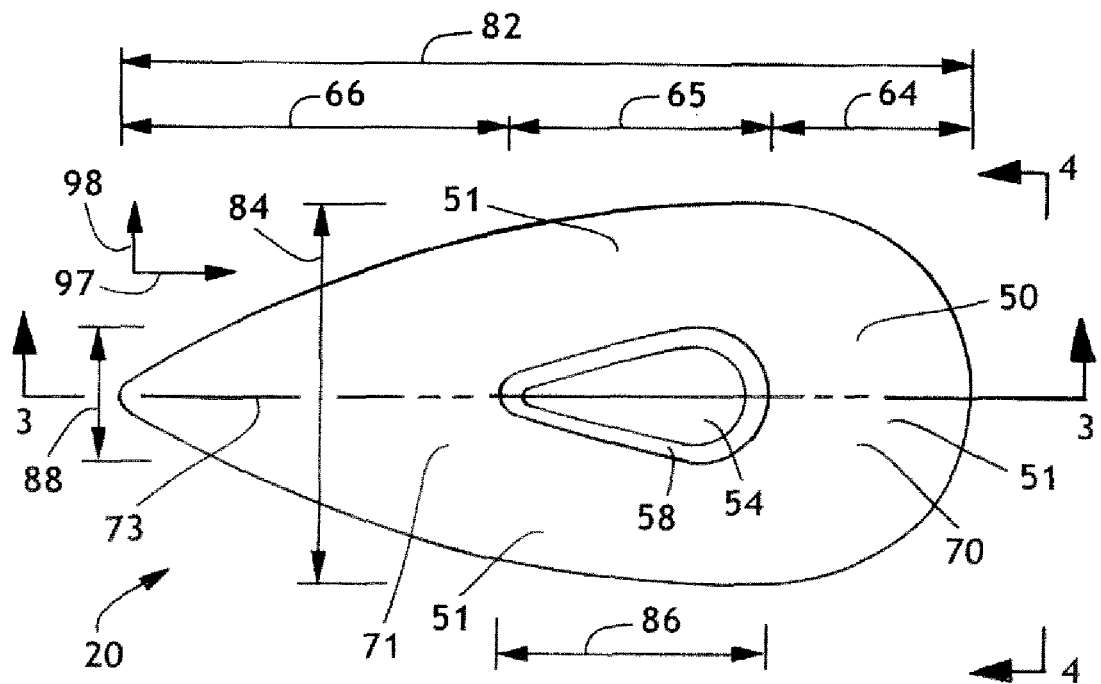
FIG. 2 illustrates a top view of the bodily exudate capturing article of FIG. 1.
Figure 3:
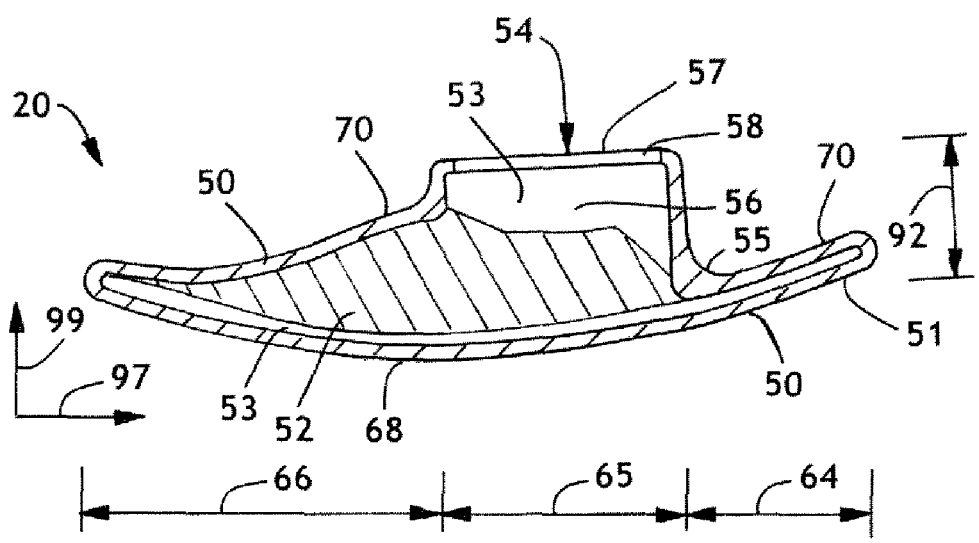
FIG. 3 illustrates a cross-sectional view of the bodily exudate capturing article of FIG. 2 taken along line 3-3.

Referring now to FIGS. 1-4, FIG. 1 representatively illustrates a side view of one embodiment of the present invention. FIG. 2 representatively illustrates a top view of the embodiment of FIG. 1. FIG. 3 representatively illustrates a cross sectional view of the intralabial urinary incontinence article 20 of FIGS. 1 and 2 taken along line 3-3 of FIG. 2.

Figure 4:
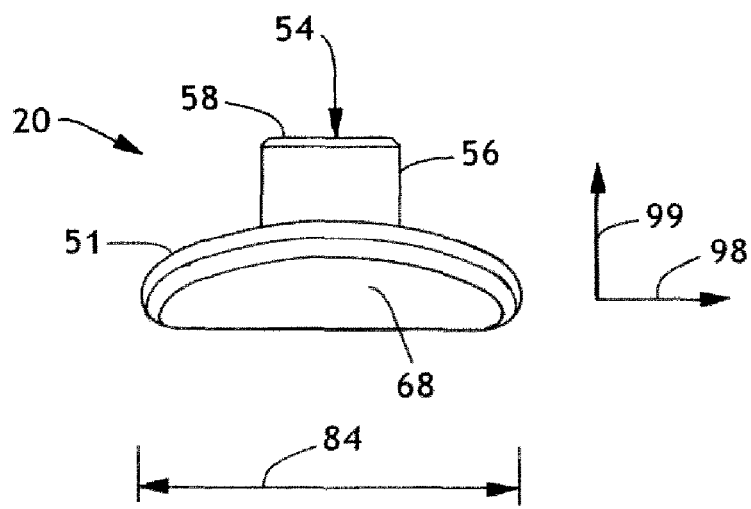
FIG. 4 illustrates an anterior end view of the bodily exudate capturing article of FIG. 2 taken along line 4-4.

FIG. 4 representatively illustrates an anterior end view of the embodiment of FIGS. 1 and 2 taken along line 4-4 of FIG. 2. The intralabial urinary incontinence article, shown generally at 20, defines a longitudinal axis 97, a transverse axis 98, and a z-axis 99. As viewed along the longitudinal axis 97, the intralabial urinary incontinence article 20 is composed of an anterior portion 64, a central portion 65 and a posterior portion 66. As used herein, the term "anterior" refers to the direction towards the front of the wearer during use. As used herein, the term "posterior" refers to the direction towards the back of the wearer during use. The central portion 65 connects the anterior portion 64 and the posterior portion 66. The shape of the intralabial urinary incontinence article 20 is generally defined by an exostructure 50 which defines at least one internal space 53. In various embodiments, the internal space 53 may include an absorbent 52 as representatively illustrated by cross hatch in FIG. 3. The intralabial urinary incontinence article 20 has a top surface 70 and a bottom surface 68. As used herein, the term "top surface" refers to that surface that is directed generally towards the wearer during use. The top surface 70 is primarily in contact with the skin of the wearer during use. As used herein, the term "bottom surface" refers to a surface facing generally away from the wearer during use. The bottom surface 68 is primarily oriented towards a covering garment, for example underwear, of the wearer during use. At least a portion of the exostructure 50 further defines a flange 51. The flange 51 has a length 82 generally along the longitudinal axis 97 and a width 84 generally along the transverse axis 98. The flange 51 is adapted to rest at least partially outside the labia of a female wearer as representatively illustrated in FIGS. 7A-C.

The exostructure 50 yet further defines a neck 56 extending from the top surface 70 in the z-axis direction 99. The neck 56 has a height 92, a proximal end 55 and a distal end 57. The neck 56 defines a fluid receiving opening 54 located generally at the distal end 57. The fluid receiving opening 54 is in communication with the internal space 53 as representatively illustrated in FIG. 3. As used herein, the term "communication" means to connect or open into. In various embodiments, the neck 56 and the fluid receiving opening 54 may be located in the anterior portion 64, the posterior portion 66, the central portion 65, or may be located at least partially in two or more portions thereof. The fluid receiving opening 54 has a length 86 and a width 88 as representatively illustrated in FIG. 2. The fluid receiving opening 54 may, in various embodiments, include a defining ring 58. The defining ring 58 may partially or completely circumscribe the fluid receiving opening 54. As illustrated in FIG. 2, the representative embodiment shows a defining ring 58 fully circumscribed about the fluid receiving opening 54.

Figure 5:
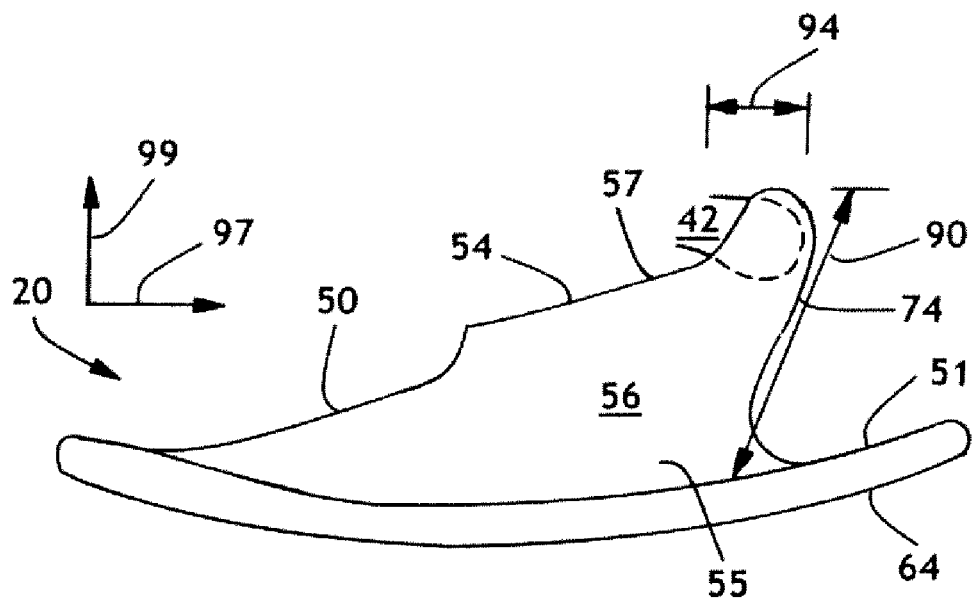
FIG. 5 illustrates a side view of an alternative embodiment of an exemplary bodily exudate capturing article.
Figure 6:
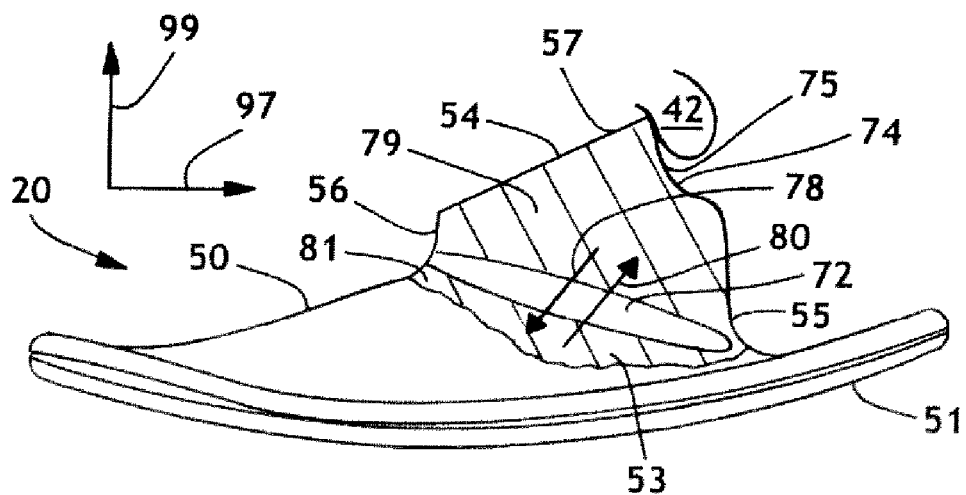
FIG. 6 illustrates a side plan view of an alternative embodiment of an exemplary bodily exudate capturing article with a section partially cut away to illustrate internal features of various embodiments.

In various embodiments, the intralabial urinary incontinence article 20 may further comprise a clitoral guide 74 as representatively illustrated in FIGS. 5 and 6. In FIG. 5, the neck 56 is elongated and curved towards the anterior portion 64 of the intralabial urinary incontinence article 20 at the distal end 57 to accept a wearer's clitoris 42 and rest at least partially upon the prepuce of clitoris 48. Using the clitoris 42 as a semi-external landmark increases the likelihood that the intralabial urinary incontinence article 20, and specifically the fluid receiving opening 54, will be properly positioned within the vestibule 24 with respect to the urethral meatus 41 of the wearer during use. Accurate placement of the intralabial urinary incontinence article 20 allows for smaller and more discreet articles to be used while still ensuring the fluid receiving opening 54 is positioned proximate the urethral meatus 41 to receive urine when released from the body of the wearer. FIG. 7B representatively illustrates one embodiment of the present invention positioned for use including a clitoral guide 74 surrounding the clitoris 42 and in contact with the prepuce of clitoris 48. A second embodiment utilizing a clitoral guide 74 is representatively illustrated in FIG. 6, wherein a portion is cutaway to reveal internal structures. In this embodiment, the neck 56 has a notch 75 at the distal end 57. The notch 75 is configured to abut the clitoris 42 thus properly positioning the intralabial urinary incontinence article 20, and specifically the fluid receiving opening 54, relative to the wearer's urethral meatus 41. This embodiment uses the clitoris 42 as a semi-external landmark to increase the likelihood that the intralabial urinary incontinence article 20 will be properly positioned within the vestibule 24 of the wearer during use. FIG. 7C representatively illustrates one embodiment of the present invention positioned for use including a clitoral guide 74 abutting the clitoris 42. The intralabial urinary incontinence article 20 is generally adapted to fit in the genital area of a female user as representatively illustrated in FIGS. 7A, 7B, and 7C. The neck 56 of the intralabial urinary incontinence article 20 is adapted to fit between the labia majora 22 and the labiaminora 23 and reside at least partially in the vestibule 24 such that the fluid receiving opening 54, the defining ring 58, or both are proximate and/or at least partially in contact with the vestibule floor 30 of the wearer during use. The fluid receiving opening 54, the defining ring 58, or both are adapted to surround the urethral meatus 41 from which urine flows during episodes of incontinence. When urine is released, it passes through the fluid receiving opening 54, through the neck 56 and is directed by gravity and/or by capillary action towards the internal space 53 contained within the exostructure 50. In various embodiments, the urine may be directed towards an absorbent 52 disposed at least partially within the internal space 53. The neck height 92 generally determines the position of the fluid receiving opening 54 relative to the vestibule floor 30. In various embodiments, the fluid receiving opening 54 of the intralabial urinary incontinence article 20 is adapted to reside within about 36 mm, about 28 mm, about 24 mm, about 21 mm, or about 16 mm of at least a portion of the vestibule floor 30. In other embodiments, the fluid receiving opening 54 is adapted to reside within about 24 mm, about 18 mm, about 16 mm, about 14 mm, or about 11 mm of at least a portion of the vestibule floor 30. In other embodiments, the fluid receiving opening 54 is adapted to reside within about 12 mm, about 10 mm, about 8 mm, about 7 mm, or about 5 mm of at least a portion of the vestibule floor 30. In other embodiments, the fluid receiving opening 54 is adapted to reside within about 6 mm, about 5 mm, about 4 mm, about 3 mm, or about 2 mm of at least a portion of the vestibule floor 30. In yet other embodiments, the fluid receiving opening 54 is adapted to contact at least a portion of the vestibule floor 30.

In various embodiments the exostructure 50 may be fluid impervious to protect the wearer's body from wetness. In such embodiments, the captured urine and other bodily exudates are isolated from the skin of the wearer thereby minimizing the discomfort associated with a saturated article against the skin. The isolation of urine and other exudates also minimizes the skin health issues that accompany prolonged exposure to urine and other exudates. The exostructure 50 can generally be constructed of silicone, polyurethanes, closed cell foam, biomedical polyurethane, biomedical silicones, biodegradable polymers, open cell foam with an external sealant or poly sack, hydrogel, temperature sensitive polymeric material, ion sensitive material, bioelastic polypeptide polymers, natural rubber or other suitable materials or combinations thereof. In various embodiments, the exostructure 50 can be constructed of a resilient material or materials. As used herein, the term "resilient" describes a material that is capable of recovering at least a portion of its size, shape, and structural proportion after deformation caused by a compressive stress. An example of a resilient material suitable for the exostructure 50 includes a silicone composite such as a silicone elastomer sold under the trade name MED-4015 or MED-4016 available from NuSil Technology having offices at 1050 Cindy Lane, Carpinteria, Calif., 93013. In other embodiments, the exostructure 50 may result in an intralabial urinary incontinence article 20 that is crush resistant. As used herein, the term "crush resistant" refers to a structure that preserves the internal space 53 in whole or in part after an external force is applied. For example, a structure would be considered crush resistant if it retained at least about 50% of its original volume after an external force is applied. In the embodiments herein, the external forces can result from a wearer sitting upon the intralabial urinary incontinence article 20 during use, or the force applied by a wearer's legs closing about the intralabial urinary incontinence article 20, or the force applied by the wearer during the insertion and positioning of the intralabial urinary incontinence article 20 into the vestibule 24, or the force applied by a wearer's labia, or combinations thereof. One suitable material for manufacturing a crush resistant intralabial urinary incontinence article 20 is, for example, biomedical polyurethanes and/or biomedical silicones. Suitable polyurethanes may be open cell or closed cell foams. The exostructure 50 may also be made expandable. As used herein, the term "expandable" refers to a structure made from a material that distends or increases in size or volume as a result of pressure from within. An example of an expandable material suitable for use in the exostructure 50 includes, but is not limited to, open cell or closed cell foams, silicones, and polyurethanes.

As discussed above, the exostructure 50 provides the shape of the intralabial urinary incontinence article 20 and defines an internal space 53. The internal space 53 has a volume and may contain an absorbent 52. The volume of internal space 53 can range from less than about 1 milliliter (ml) to about 50 ml. In embodiments wherein the exostructure 50 is expandable, the volume of the internal space 53 may increase upwards to 60, 70, 80, 90, 100, 110, 120, 130, 140, or 150 milliliters as fluid is captured within the internal space 53 of the intralabial urinary incontinence article 20 or when fluid is captured within the absorbent 52 within the internal space 53.

Also, as previously discussed, the exostructure 50 defines a flange 51. The flange 51 may be shaped and dimensioned in various configurations to cooperate with the female anatomy. As generally illustrated in FIG. 1, the flange 51 has a generally arcuate shape bending towards the top surface 70 in both the anterior portion 64 and the posterior portion 66. In various embodiments, the curvature of the flange 51 may be greater or lesser but generally is configured to cooperate with the natural curvature of a female wearer's anatomy. Referring to FIG. 2, the flange 51 has a generally tear-drop shape and rounded edges. In the illustrated embodiment, the flange 51 has a larger radius of curvature in the anterior portion 64 than in the posterior portion 66. This general shape is configured to coordinate with the natural shape of a wearer's vaginal, labial, and perineal areas. For example, the flange 51 may have a sloped area 71 on the top surface 70 in the posterior portion 66 to accommodate the region between the posterior commissure of labia 44 and the anus 34. The sloped area 71 may be downwardly sloping along the longitudinal axis 97 starting at a point adjacent the neck 56 and continuing towards the posterior portion 66 as representatively illustrated in FIG. 1. The sloped area 71 may also be downwardly sloping along the transverse axis 98 as representatively illustrated in FIG. 2. The embodiment illustrated in FIG. 2 shows the sloped area 71 peaking along a center line 73 generally parallel with longitudinal axis 97 and downwardly sloping away from the center line 73 in the transverse axis 98.

The flange 51 has a length 82 in the longitudinal direction 97 and a width 84 in the transverse direction 98 as representatively illustrated in FIG. 2. In various embodiments, the length 82 of the flange 51 may be about 103 mm to about 115 mm, or about 107 mm to about 114 mm, or about 111 mm. In other embodiments, the length 82 of the flange 51 may be about 46 mm to about 94 mm, or about 60 mm to about 75 mm, or about 66 mm. In yet other embodiments, the length 82 of the flange 51 may be about 25 mm to about 67 mm, or about 35 mm to about 53 mm, or about 44 mm. In various embodiments, the length 82 of the flange 51 is configured to generally span from a wearer's prepuce of clitoris 48 to a wearer's perineum 32. The width 84 of the flange 51 may be from about 36 mm to about 75 mm, or about 47 mm to about 62 mm, or about 54 mm. In general, the width 84 of the flange 51 is configured to fit between a wearer's legs and to fit at least partially within a wearer's labia.

The exostructure 50 yet further defines a neck 56 extending from the top surface 70. The neck 56 has a height 92 as measured along the z-axis 99, a proximal end 55 and a distal end 57. The neck defines a fluid receiving opening 54 located generally at the distal end 57. The fluid receiving opening 54 is in communication with the internal space 53 as representatively illustrated in FIG. 3. FIGS. 1, 3, 5, and 6 representatively illustrate an intralabial urinary incontinence article 20 with a neck 56 located generally in the central portion 65 of the article 20. However, the neck 56 may be located at least partially in the anterior portion 64, posterior portion 66, central portion 65, or combinations thereof. The neck height 92 may be about 5 mm to about 70 mm, about 10 mm to about 65 mm, 27 mm to about 60 mm, about 35 mm to about 46 mm, or about 40 mm. In various other embodiments, the neck height 92 may be about 5 mm to about 45 mm, about 15 mm to about 50 mm, about 25 mm to about 40 mm, or about 30 mm. In general, the length 92 of the neck 56 is configured to position the fluid receiving opening 54 proximate the urethra meatus 41 during use by a wearer.

The fluid receiving opening 54 is dimensioned and adapted to surround a wearer's urethral meatus 41 and to directly capture urine as it is discharged from the body of the wearer. The fluid receiving opening 54 has a length 86 along the longitudinal axis 97 and a width 88 along the transverse axis 98 as representatively illustrated in FIG. 2. The length 86 may be from about 25 mm to about 67 mm, from about 35 mm to about 53 mm, or about 44 mm. In other embodiments, the length 86 of the fluid receiving opening 54 may be from about 9 mm to about 36 mm, from about 15 mm to about 25 mm, or about 20 mm. In various embodiments, the length 86 is configured to at least span the urethral meatus 41 and allow for movement of the intralabial urinary incontinence article 20 within a wearer's vestibule 24 along the longitudinal axis 97 while still spanning the urethral meatus 41. In embodiments with a greater length 86, the fluid receiving opening 54 may be adapted to also span a wearer's vaginal orifice 38 and thereby allow for the direct capture of vaginal discharge, menses, and other bodily exudates in addition to urine. The width 88 of fluid receiving opening 54 may be from about 5 mm to about 25 mm, from about 10 mm to about 15 mm, or about 10 mm. The width 88 is configured to span the urethral meatus 41 and allow for movement of the intralabial urinary incontinence article 20 within a wearer's vestibule 24 along the transverse axis 98 while still spanning the urethral meatus 41. The fluid receiving opening 54 is proximate the floor of the vestibule 30 during use as representatively illustrated in FIGS. 7A, 7B, and 7C. The fluid receiving opening 54 may be at least partially in contact with the floor of the vestibule 30 during use. It is believed that locating the fluid receiving opening 54 proximate to and circumjacent to the urethral meatus 41 minimizes urine leakage during use. It is also believed that directing urine through fluid receiving opening 54 into internal space 53 results in less leakage because the volume of internal space 53 can more easily accommodate a surge of urine than can a traditional intralabial article receiving urine on the surface. In traditional intralabial articles, the fluid is not immediately contained and must be absorbed through the surface of the article before the fluid runs off the surface of the article resulting in a leak.

While the illustrations generally show the fluid receiving opening 54 as having generally the same dimensions along the longitudinal axis 97 and transverse axis 98 as the neck 56, the invention herein also contemplates embodiments wherein the fluid receiving opening 54 is larger than the neck 56 (i.e., the neck 56 could flare at the distal end 57 to define a larger fluid receiving opening 54). In other embodiments, the fluid receiving opening 54 may be smaller than the neck 56 (i.e., the neck 56 could narrow at the distal end 57 to define a smaller fluid receiving opening 54).

The fluid receiving opening 54 may have various shapes in different embodiments, such as, for example, oval, circle, ovoid, or other suitable shapes adapted to fit at least partially within a wearer's vestibule and allow urine to pass through. FIG. 2 representatively illustrates the fluid receiving opening in a generally teardrop-shaped configuration. It is believed that a teardrop shape coordinates well with the natural shape of the vestibule 24 as illustrated in FIG. 8 but other suitable shapes are contemplated as within the scope of this invention. The fluid receiving opening 54 is oriented to place the larger end of the teardrop shape towards the anterior portion 64 of the intralabial urinary incontinence article 20 to better cooperate and surround with the urethral meatus 41. In addition, the teardrop shape allows for anterior to posterior movement as well as posterior to anterior movement of the intralabial urinary incontinence article 20 during use while maintaining the urethral meatus 41 within the fluid receiving opening 54.

Referring to FIGS. 2, 3 and 4, the fluid receiving opening 54 may include a defining ring 58 circumscribed about the fluid receiving opening 54. The defining ring 58 may be an integral part of the neck 56 of the exostructure 50 or may be a separate piece operatively joined to the neck 56 at the distal end 57. As used herein, the term "integral part" means an operation is worked upon the exostructure 50 in such a way as to form the defining ring 58. For example, the defining ring 58 could be formed by rolling the distal end 57 of the neck 56 either inward or outward. Alternatively, the intralabial urinary incontinence article 20 may be manufactured such that the exostructure 50 is thicker or denser in the defining ring 58 than in the neck 56. As used herein, the term "operatively joined" means that the defining ring 58 and the exostructure 50 may be attached or affixed in any suitable manner that permits or allows them to perform the intended or described function of the joining. The joining, attaching, connecting or the like may be either directly, such as joining either member directly to an element, or may be indirectly by means of another member disposed between the first member and the first element. For example, the defining ring 58 may be attached to the distal end 57 of the neck 56 by adhesives, thermal bonding, ultrasonic bonding or any other suitable means.

The defining ring 58 may be rigid, semi-rigid, or pliable. In various embodiments of the present invention, the defining ring 58 may be more rigid than the exostructure 50. In such embodiments, the defining ring 58 can prevent the labia majora 22 and labiaminora 23 from crushing or partially crushing the fluid receiving opening 54, thus maintaining a passage through which urine can pass unhindered into the internal space 53 of the intralabial urinary incontinence article 20. In various embodiments, the urine can pass into the internal space 53 and an absorbent 52 disposed therein. The combination of a more rigid defining ring 58 and a less rigid exostructure 50 allows the exostructure 50 to conform to the shape and movement of the user while keeping the fluid receiving opening 54 from collapsing. In various other embodiments, the defining ring 58 may have "spring-like" qualities in that the defining ring 58 may be compressed during insertion into the vestibule 24 and produce an opposite force upon release of the compressing force thus "springing" to the contours of the vestibule 24. The defining ring 58 may also be adapted to provide lateral force during use and thus "anchor" the intralabial urinary incontinence article 20 in position. An improved anchor may allow for greater exudate capture while minimizing the risk of the intralabial urinary incontinence article 20 becoming dislodged before being removed.

In embodiments including a clitoral guide 74, the dimensions of the clitoral guide 74 may vary depending on whether the clitoral guide 74 is adapted to envelope a wearer's clitoris 42 as representatively illustrated in FIGS. 5 and 7B or whether the clitoral guide 74 is adapted to abut the clitoris 42 as representatively illustrated in FIGS. 6 and 7C. Referring now to FIG. 5, the clitoral guide 74 has a guide height 90 and a guide length 94. The guide height 90 may be about 37 mm to about 84 mm, or about 49 mm to about 66 mm, or about 57 mm. The guide length 94 may be about 25 mm to about 59 mm, or about 35 mm to about 48 mm, or about 40 mm.

In various embodiments, the intralabial urinary incontinence article 20 may include a one-way valve 72 within the internal space 53 as representatively illustrated in FIG. 6. The embodiment illustrated in FIG. 6 has part of the exostructure 50 cut away to illustrate internal structures. The one-way valve 72 may span the neck 56 at various locations and is shown here towards the proximal end 55 of the neck 56. The one-way valve 72 divides the internal space 53 into at least one first region 79 and at least one second region 81. The one-way valve 72 allows fluid within the internal space 53 to pass from the first region 79 into the second region 81 in the direction indicated by arrow 78. The one-way valve 72 prevents fluid in the second region 81 from passing into the first region 79 in the direction indicated by arrow 80. In various embodiments, the first region 79, the second region 81, or both may contain an absorbent 52.

In various embodiments, the internal space 53 of intralabial urinary incontinence article 20 may include an absorbent 52. The absorbent 52 may be any material which is capable of absorbing and containing body exudates, particularly urine. The absorbent 52 can be manufactured from a variety of liquid-absorbent materials commonly known in the disposable absorbent article art. For example, absorbent materials such as cellulose fibers, wood pulp, regenerated cellulose or cotton fibers can be used. Such fibers may be chemically or physically modified. The absorbent 52 may include any of the above fibers in combination with other materials, both natural and synthetic, such as hydrophilic foams, hydrophilic polymers, films or the like. The absorbent 52 may also include a foam-reinforced fibrous network such as that described in U.S. Pat. No. 6,261,679 issued on Jul. 17, 2001 to Chen et al., the disclosure of which is incorporated herein and made a part hereof. Wood pulp is frequently the material of choice primarily because it is inexpensive and readily available. The absorbent 52 may also include a thin absorbent layer of material such as tissue, fabric or the like made of cellulosic fibers. The absorbent 52 can be or can include one or more superabsorbent materials known in the art. By "superabsorbent" we mean a hydrocolloid material that is capable of absorbing an amount of water which is at least ten times the weight of the hydrocolloid particles in the dry form and preferably from about 15 to 70 times the dry weight. Such materials are further described in U.S. Pat. No. 5,247,072 issued on Sep. 21, 1993 to Ning et al., the disclosure of which is incorporated herein and made a part hereof.

While the intralabial urinary incontinence article 20 is designed to be used once and then discarded, as noted above, removal, emptying and repositioning the intralabial urinary incontinence article 20 may be considered a single use. The present invention contemplates an exostructure 50 that may be positioned a limited number of times, for example 2, 3, or 4 times, during a limited period of time, for example 24 hours, before being discarded. Also, the absorbent 52 may be removable, replaceable, and disposable. In such embodiments, the wearer or caregiver removes an intralabial urinary incontinence article 20 containing an absorbent 52 from a wearer's vestibule 24 after use. The used absorbent 52 is removed from the exostructure 50 and discarded. An unused absorbent 52 is then inserted into the internal space 53 of the exostructure 50 and the intralabial urinary incontinence article 20 is repositioned at least partially within the wearer's vestibule 24 to capture urine released from the body. Alternatively, the intralabial urinary incontinence article 20 containing an absorbent 52 is removed after use, the absorbent 52 is removed from the exostructure 50, and the intralabial urinary incontinence article 20 is repositioned without an absorbent 52. In yet another alternative, an intralabial urinary incontinence article 20, not containing an absorbent 52, is removed, emptied, and an absorbent 52 is inserted into the internal space 53 of the exostructure 50 before repositioning. In yet another alternative, the intralabial urinary incontinence article 20, not containing an absorbent 52, is removed, emptied, and repositioned, without adding an absorbent 52.

In various embodiments of the present invention, the intralabial urinary incontinence article 20 may be at least partially covered by a shroud (not shown). In various embodiments, the shroud may cover the entire exterior surface of intralabial urinary incontinence article 20. In other embodiments, the shroud may only cover the bottom surface 68 or only the top surface 70, or combinations thereof. In yet other embodiments, the shroud may only cover the fluid receiving opening 54, the neck 56, or combinations thereof. Examples of materials suitable for the shroud include a wide selection of web materials, such as foams, plastic films or natural or synthetic fibers. Other possible materials are webs made from synthetic fibers, such as polyester or polypropylene fibers, or a combination of natural and synthetic fibers. For example, neck bonded spunbond material can be used for the shroud. The shroud may be composed of a substantially hydrophobic material or substantially hydrophilic material. The shroud may be necked or creped or otherwise formed to provide extensibility in at least one direction. Further, the shroud may optionally be composed of a microporous material which permits vapors to escape through the shroud while preventing liquid exudates from passing through. In various embodiments, the shroud may be attached to the intralabial urinary incontinence article 20 by any suitable bonding means, such as, for example, thermal bonding, adhesive bonding, ultrasonic bonding or combinations thereof. In other embodiments, the shroud may not be connected to the exostructure 50, but may instead at least partially encase the intralabial urinary incontinence article 20.

In various embodiments, the intralabial urinary incontinence article 20 may be secured to the body of the user through friction, adhesives, tension created by the defining ring 58, belts, undergarments, or other suitable attachment means or combinations thereof. In embodiments including adhesives, the intralabial urinary incontinence article 20 may include a body adhesive to at least partially secure the article 20 to the body of the user. In embodiments including a shroud, the adhesive can be deposited on the shroud facilitating contact with the user's skin. The adhesive may be applied to the top surface 70 such that contact is made with the skin of the user upon insertion of the intralabial urinary incontinence article 20 into the interlabial region. In other embodiments, the intralabial urinary incontinence article 20 may also include an adhesive on the bottom surface 68 such that contact is made with the clothing of the user. In yet other embodiments, the intralabial urinary incontinence article 20 may include adhesive on at least a portion of both the top surface 70 and the bottom surface 68. One suitable adhesive is described in U.S. Pat. No. 6,213,993 issued Apr. 10, 2001 to Zacharias et al., the disclosure of which is incorporated herein and made a part hereof.

In various embodiments, the intralabial urinary incontinence article 20 may include a wetness indicator (not shown). The wetness indicator may included a pH change or color change indicator material that is either integrated with the exostructure 50 or that is partially or entirely covering the surface of the exostructure 50. The indicator material can change color upon contacting the wetness from the internal space 53, the absorbent 52, or both. An example of a suitable color change indicator is disclosed in U.S. Pat. No. 6,297,424 to Olson et al., issued Oct. 2, 2001, the entirety of which is incorporated by reference.

The wetness indicator may include an actuating member connected to the intralabial urinary incontinence article 20 in liquid communication with the absorbent 52 or the internal space 53 composed of a liquid-contractible material. The liquid-contractible material is capable of shrinking upon contact with water while maintaining a substantially unitary configuration. An indicating means is connected to the actuating member for designating a wetness condition of the absorbent body, and is translatable along a selected path in response to the shrinkage of the actuating member.

The wetness indicator may alternately be a tactile wetness indicator wherein a portion of the exostructure 50 is thin and pliant. In such embodiments, the absorbent 52 expands upon absorption of urine causing the thin portion of the exostructure 50 to bulge. Alternatively, fluid captured in the internal space 53 may cause the thin portion of the exostructure 50 to bulge. In either situation, the bulge is physically detectable indicating the presence of urine or other bodily exudates in the intralabial urinary incontinence article 20.

In yet other embodiments, the intralabial urinary incontinence article 20 may include a wetness indicator that provides a thermal indication when urine is present. The thermal indication can either be an increase or a decrease in temperature.

While the invention has been described in detail with respect to specific embodiments thereof, it will be appreciated that those skilled in the art, upon attaining an understanding of the foregoing may readily conceive of alterations to, variations of and equivalents to these embodiments. Accordingly, the scope of the present invention should be assessed as that of the appended claims and any equivalents thereto.

We claim:

1. A disposable intralabial urinary incontinence article comprising:
   a resilient and liquid impermeable exostructure defining a top surface and an internal space adapted to receive and capture fluids;
   at least a portion of the exostructure further defining a flange adapted to rest at least partially outside the labia of a female wearer wherein the flange is configured to span from the prepuce of clitoris to the perineum of the wearer;
   the exostructure yet further defining a neck extending from the top surface and adapted to at least partially occupy a vestibular region of the wearer and rest proximate the wearer's vestibule floor;
   the neck defining a fluid receiving opening in communication with the internal space and wherein the neck is configured so the fluid receiving opening is positioned generally adjacent the wearer's urethral meatus to direct urine into the internal space.

2. The disposable intralabial urinary incontinence article of claim 1, wherein the fluid receiving opening is at least partially circumscribed by a defining ring wherein the defining ring and the fluid receiving opening have a generally teardrop-shaped configuration.

3. The disposable intralabial urinary incontinence article of claim 2, wherein the defining ring is resilient and is adapted to resist labial crushing and wherein the defining ring is adapted to provide lateral force and anchor the intralabial urinary incontinence article in position.

4. The disposable intralabial urinary incontinence article of claim 1 further comprising a body adhesive.

5. The disposable intralabial incontinence article of claim 1, further comprising a one-way valve disposed within the internal space of the exostructure dividing the internal space into a first region and a second region and wherein the one-way valve is adapted to allow fluid to pass from the first region into the second region and is also adapted to prevent fluid from passing from the second region into the first region and wherein the second region includes an absorbent.

6. The disposable intralabial incontinence article of claim 1 wherein the neck comprises a clitoral guide adapted to coordinate with a wearer's clitoris and assist the wearer to properly position the neck so the fluid receiving opening is generally adjacent the wearer's urethral meatus.

7. The disposable intralabial incontinence article of claim 6 wherein the clitoral guide is an extension of the neck and is adapted to surround the clitoris and rest in contact with the wearer's prepuce of clitoris.

8. The disposable intralabial incontinence article of claim 6 wherein the neck further includes a notch and the notch is the clitoral guide adapted to abut the wearer's clitoris.

9. The disposable intralabial incontinence article of claim 1, further comprising an absorbent disposed within the internal space of the liquid impermeable exostructure.

10. The disposable intralabial incontinence article of claim 9, wherein the absorbent comprises cellulose, super absorbent polymer, open cell foam, open cell polymeric foam, absorbent polymer films, or combinations thereof.

11. The disposable intralabial incontinence article of claim 1 wherein the top surface has a sloped area in the posterior portion to accommodate the region between the posterior commissure of labia and the anus; wherein the sloped area is downwardly sloping along a longitudinal axis starting at a point adjacent the neck and continuing towards the posterior portion.

12. The disposable intralabial incontinence article of claim 11 wherein the article defines a centerline and the sloped area of the top surface peaks along the centerline and downwardly slopes away from the center line in both directions along the transverse axis.

13. A disposable intralabial urinary incontinence article comprising:
   a resilient and liquid impermeable exostructure defining a top surface and an internal space adapted to receive and capture fluids;

at least a portion of the exostructure further defining a flange adapted to rest at least partially outside the labia of a female wearer;

the exostructure having an anterior portion width greater than a posterior portion width;

the top surface of the exostructure in the posterior portion having a sloped area to accommodate the region between the posterior commissure of labia and anus;

the exostructure yet further defining a neck extending from the top surface and adapted to at least partially occupy a vestibular region of the wearer and rest proximate the wearer's vestibule floor;

the neck defining a fluid receiving opening in communication with the internal space, wherein the fluid receiving opening spans the wearer's urethral meatus and vaginal orifice to capture vaginal discharge, menses, urine, or other bodily exudates and wherein the neck is configured so the fluid receiving opening is positioned generally adjacent the wearer's urethral meatus to direct urine into the internal space; wherein the fluid receiving opening is at least partially circumscribed by a defining ring.

14. The disposable intralabial urinary incontinence article of claim 13 further comprising an absorbent disposed within the internal space of the liquid impermeable exostructure.

15. The disposable intralabial incontinence article of claim 13 wherein the neck comprises a clitoral guide adapted to coordinate with a wearer's clitoris and assist the wearer to properly position the neck so the fluid receiving opening is generally adjacent the wearer's urethral meatus.

16. The disposable intralabial incontinence article of claim 13 wherein the article defines a centerline and the sloped area of the top surface peaks along the centerline and downwardly slopes away from the centerline in both directions along the transverse axis.

17. A disposable intralabial urinary incontinence article comprising:

a resilient and liquid impermeable exostructure defining a top surface and an internal space adapted to receive and capture fluids;

an absorbent disposed within the internal space of the liquid impermeable exostructure;

at least a portion of the exostructure further defining a flange adapted to rest at least partially outside the labia of a female wearer;

the exostructure having an anterior portion width greater than a posterior portion width;

the top surface of the exostructure in the posterior portion having a sloped area to accommodate the region between the posterior commissure of labia and anus, wherein the sloped area of the top surface peaks along a centerline and downwardly slopes away from the centerline in both directions along a transverse axis;

the exostructure yet further defining a neck extending from the top surface and adapted to at least partially occupy a vestibular region of the wearer and rest proximate the wearer's vestibule floor;

the neck defining a fluid receiving opening in communication with the internal space and wherein the neck is configured so the fluid receiving opening is positioned generally adjacent the wearer's urethral meatus to direct urine into the internal space; wherein the fluid receiving opening is at least partially circumscribed by a defining ring wherein the defining ring and the fluid receiving opening have a generally teardrop-shaped configuration; wherein the neck comprises a clitoral guide adapted to coordinate with a wearer's clitoris and assist the wearer to properly position the neck so the fluid receiving opening is generally adjacent the wearers urethral meatus.

* * * * *